United States Patent [19]

Turbe et al.

[11] Patent Number: 4,457,178
[45] Date of Patent: Jul. 3, 1984

[54] PROCESS AND APPARATUS FOR TESTING OF RAILS BY ULTRASOUND

[75] Inventors: Jean-Pierre Turbe, Nantevil-les-Meaux; Bruno Meignan, Esbly both of France

[73] Assignee: Matix Industries, Inc., France

[21] Appl. No.: 362,264

[22] Filed: Mar. 26, 1982

[30] Foreign Application Priority Data

Jun. 23, 1981 [FR] France ................... 81 12334

[51] Int. Cl.$^3$ ........................................... G01N 29/04
[52] U.S. Cl. ........................................ 73/636; 73/624; 73/625; 73/628
[58] Field of Search ................... 73/624, 625, 628, 636

[56] References Cited

U.S. PATENT DOCUMENTS

| 2,875,607 | 3/1959 | Boxcer et al. ........................ 73/628 |
| 2,893,239 | 7/1959 | Renaut ................................... 73/624 |
| 4,116,074 | 9/1978 | Jensen ................................... 73/607 |

FOREIGN PATENT DOCUMENTS

| 241181 | 12/1960 | Australia ............................... 73/636 |
| 1952380 | 3/1978 | Fed. Rep. of Germany ........ 73/628 |
| 55-95860 | 7/1980 | Japan .................................... 73/628 |
| 46756 | 3/1963 | Poland ................................... 73/628 |

Primary Examiner—Howard A. Birmiel
Attorney, Agent, or Firm—Darby & Darby

[57] ABSTRACT

Beams of ultrasound are transmitted into a rail. The transmission alternates between vertical and oblique beams. Transmission of the beams and reception of ultrasonic echoes is accomplished by a probe which includes a two channel ultrasonic transducer. The echoes are displayed simultaneously on two linear arrays of LED's which are arranged to resemble the relationship between a vertical beam and an oblique beam.

13 Claims, 4 Drawing Figures

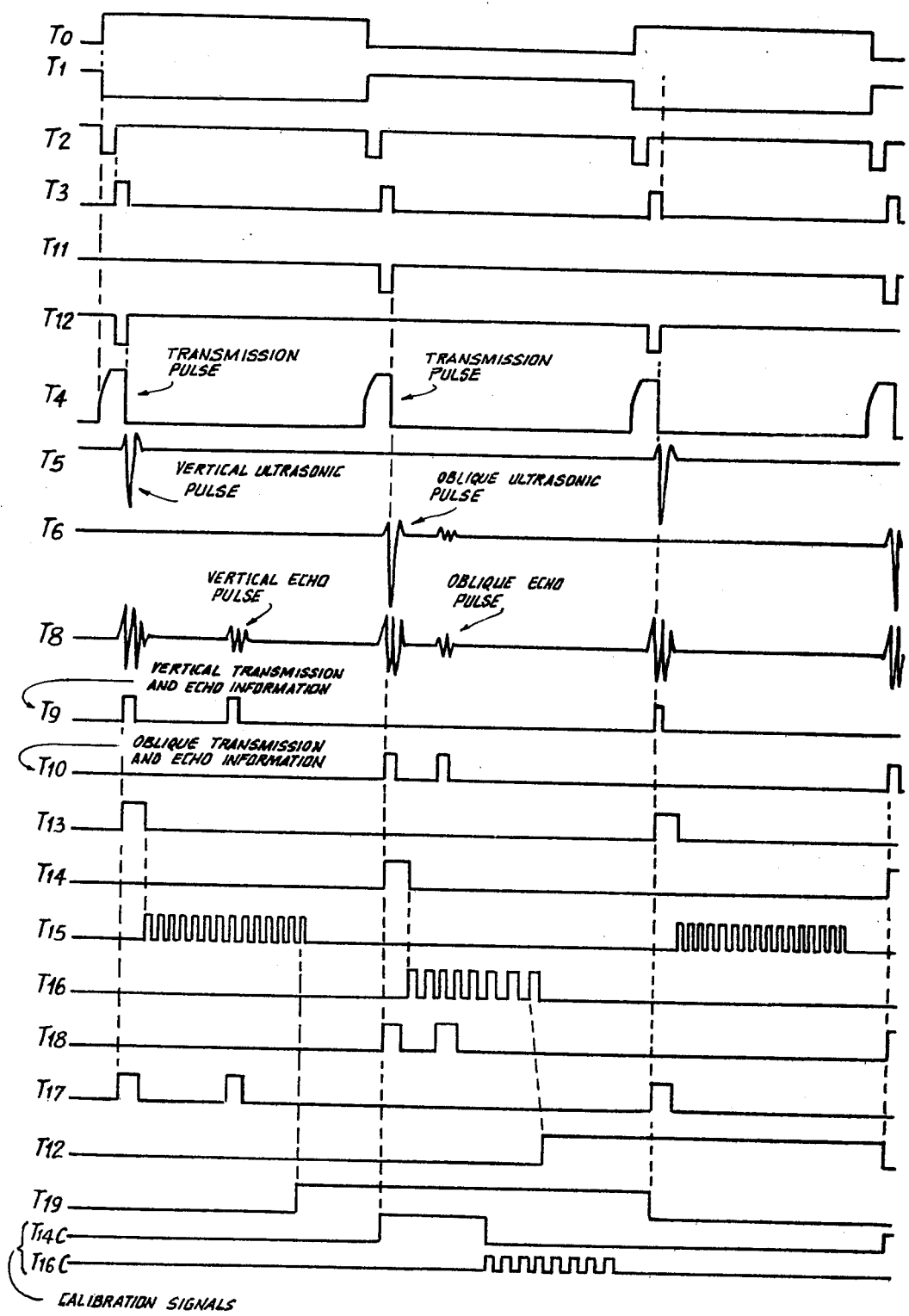

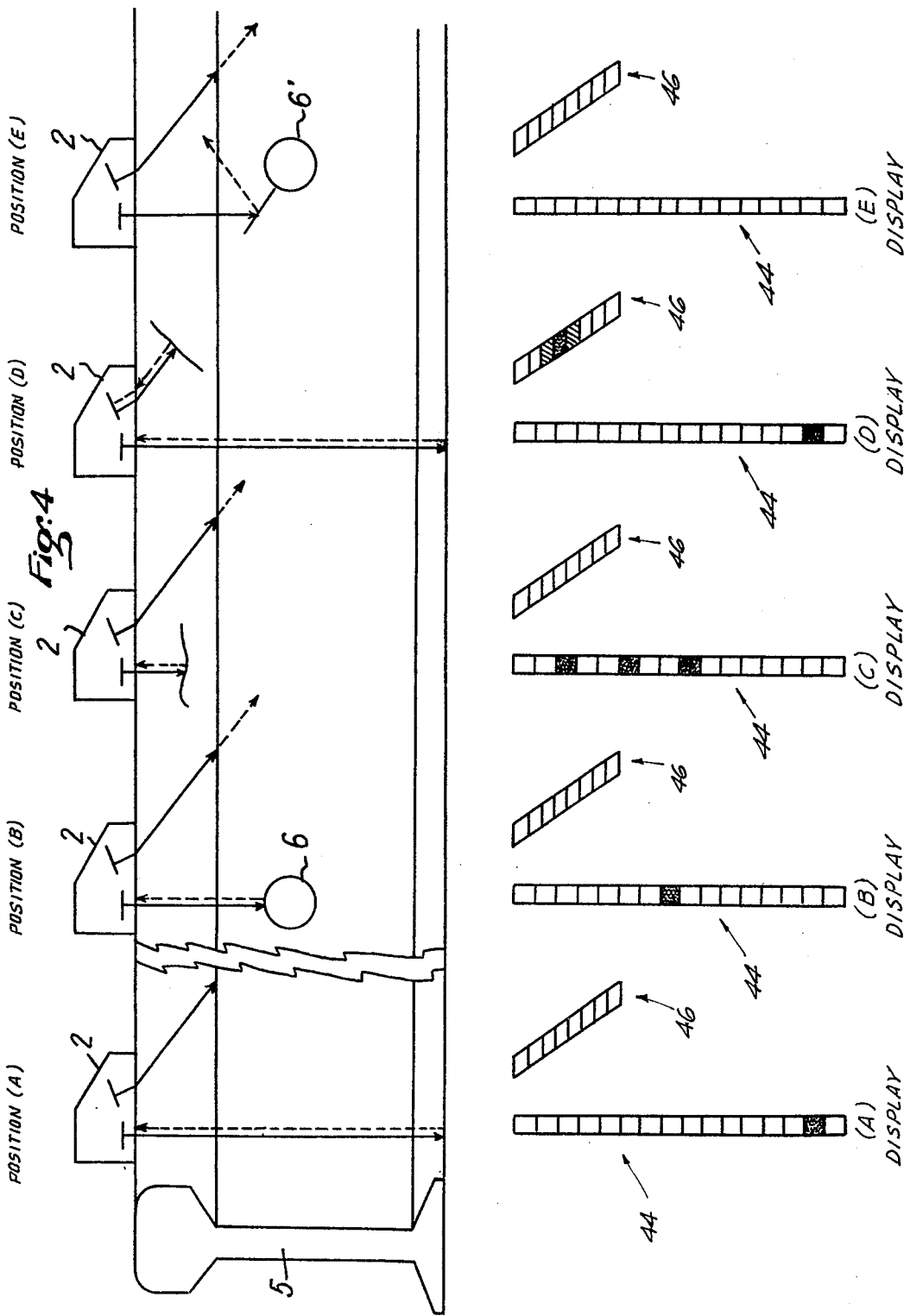

PROCESS AND APPARATUS FOR TESTING OF RAILS BY ULTRASOUND

The invention relates to a nondestructive process and apparatus for testing of rails by ultrasound.

The nondestructive testing of metal parts by ultrasound is known.

It is possible to probe a body by transmitting ultrasound pulses and by receiving ultrasonic echoes, and to pick up echo signals and/or display the said signal on a cathode screen. This technique consists of placing a sensor on the part to be probed, which sensor may either be an ultrasound transceiver or two separate sensors for transmission and reception respectively, and further consists of graphically displaying the echo signals by cathode ray tube display.

Oscillograms obtained by this technique can be representations with echo intensity on the ordinate and travel time on the abscissa. They may also show a section through the part in a schematic manner or, in a more sophisticated fashion, show a plan view of the part, by synchronizing scanning and sensor position.

In the past, the technique of probing by ultrasound echoes, with cathode ray tube graphic display, has been the one adopted for testing of rails. This method has the advantage that manipulation of the apparatus is simple, and the method offers absolute safety since ultrasound is not harmful to a user. Nevertheless, known apparatus is bulky and particularly inconvenient for use on site.

Furthermore, although this method makes it possible to know, with good precision, the location, the type and the dimensions of the flaws encountered, the interpretation of the results thus displayed on the cathode ray tube requires a very high degree of training; and it is necessary to know how to allow for differences in acoustic waves, levels of measurement, frequencies used, angles, etc.

The invention proposes a simple process and apparatus which is easy to use, which does not call for special knowledge on the part of an operator, is portable, and is both small and lightweight.

One feature of the invention is that trains of ultrasonic waves are transmitted into the rail alternately in a vertical direction and an oblique direction. The emission signals and echo signals are then picked up and processed for simultaneous display on a screen, with the echo signals displayed in the two directions of transmission.

A preferred method consists of displaying the echo signals on a screen equipped with two banks of light-emitting diodes representing the two directions of transmission, so that the numbers and the positions of the diodes fired clearly indicates (for the zone probed) the thickness of the rail and/or the presence and position of a fishplate hole and/or the position and nature of internal flaws in the rail.

Control apparatus contains a probe which is a two-channel transducer of ultrasound designed to alternately transmit trains of ultrasonic waves in a vertical direction and in an oblique direction, electronic transmission governing means and means for receiving the echo signals from the sensor, means for processing and measuring the signals and means for displaying echo signals simultaneously for the two directions of transmission.

Preferably, in this case, the display means includes a screen equipped with two arrays, each array including a plurality of light-emitting diodes (LED's) and representing one of the two directions of transmission in the rail, while the means for processing and measuring the signals is arranged to permit selective firing of the diodes so that the number and the position of the fired diodes will clearly indicate, for the zone probed, the thickness of the rail and/or the presence of a fishplate hole and/or the position and the nature of internal flaws in the rail.

BRIEF DESCRIPTION OF THE DRAWINGS

The invention will be better understood, and other features will appear on reading the description which follows and which relates to the attached drawings of a preferred but nonetheless illustrative embodiment of the invention, in which:

FIG. 3 is a chart of the various signals encountered in the circuit of in FIG. 2; and FIG. 4 shows various possible displays as a function of several positions of the sensor on a rail, schematized in the same figure.

DETAILED DESCRIPTION OF PREFERRED EMBODIMENTS

Figure 1:
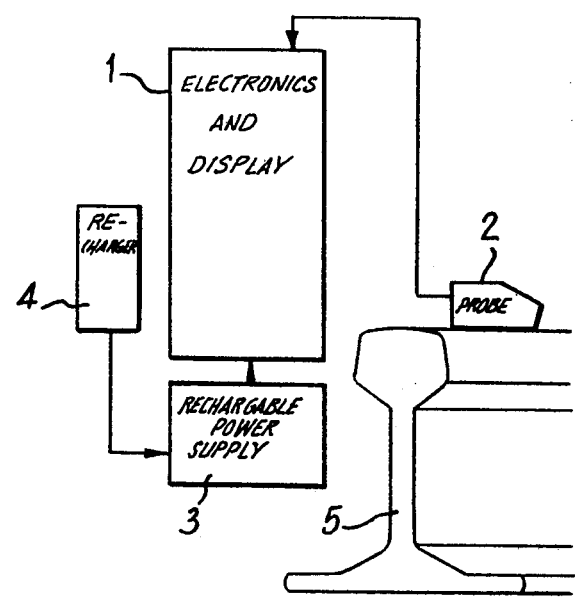
FIG. 1 schematizes the apparatus according to the invention, and its accessories.

The apparatus according to the invention, schematized in FIG. 1, has an electronic assembly 1 for its operation and for display of the results, to which is connected a probe 2 and a power supply 3 rechargeable by a recharger 4, the probe 2 being disposed on a rail schematized at 5.

The electronic part of the apparatus (FIG. 2) can be divided into three boards: transmit-receive; measurement; and display. These are separated by dashed lines, and are labelled.

The transmit-receive board contains a clock 10 which produces two logically complementary signals $T_0$ and $T_1$ (FIG. 3) Signal $T_0$ triggers a monostable (one-shot) multivibrator $M_1$ that produces two complementary output signals, of which one, $T_2$, is shaped by a monostable multivibrator $M_2$ to form signal $T_3$. Signal $T_3$ arrives at one of the two inputs on each of two NAND gates $N_1$ and $N_2$. The other inputs of NAND gates $N_1$ and $N_2$ are connected, respectively, to outputs $T_0$ and $T_1$ of clock 10.

The output signals ($T_{12}$, $T_{11}$) from gates $N_1$ and $N_2$ will operate transmitters 12 and 14 respectively. Transmitters 12 and 14 have transmitter thyristors which are triggered by signal $T_4$ from a high voltage supply 16 that is driven by the signal $T_2$ appearing at the complementary outlet of multivibrator $M_1$.

Transmitters 12 and 14 each drive one of the two channels of the probe 2. Probe 2 is hence an ultrasonic transducer which can transmit and receive ultrasonic energy from two directions. Probe 2 alternates trains of ultrasonic waves between a vertical direction driven by transmitter 12 and an oblique direction driven by transmitter 14.

The oblique direction selected here is 70°. Here the ultrasonic beams lie in a common plane, but subtend an angle of 70° of arc. By way of example, the transmission frequency in the vertical direction is 4 MHz and in the oblique direction, 2.5 MHz, while the frequency of recurrence in both directions is 150 Hz. The signals of transmission and reception for each channel, $T_5$ for the vertical beam and $T_6$ for the oblique beam are amplified by preamplifiers 18 and 20 with a single gain adjustment. The output signals from preamplifiers 18 and 20 are mixed (i.e. multiplexed) at $T_7$ and amplified by means of an amplifier 22 that produces signal $T_8$. The latter clearly shows, in the chart in FIG. 3, the signals of transmission and the echo signals.

The output from amplifier 20 is connected to two monostable multivibrators $M_3$ and $M_4$, which are clocked, respectively, by signals $T_0$ and $T_1$ from clock 10 so as to separate (i.e. demultiplex) the signals from the two channels which, after separation, become $T_9$ for the vertical beam and $T_{10}$ for the oblique beam.

The measurement board has two oscillators 24 and 26 to process the two channels individually, in view of the difference between the rates of propagation of the waves in the vertical direction (longitudinal waves) and those in the oblique direction (transverse waves). Oscillators 24 and 26 are driven indirectly by NAND gates $N_1$ and $N_2$ and signals $T_{11}$ and $T_{12}$.

Signals $T_{12}$ and $T_{11}$ are delayed by monostable multivibrators $M_5$ and $M_6$, respectively, and are transformed into transmission gate signals $T_{13}$ and $T_{14}$. The time delay is necessary because probe 2 is protected by a plastic sheet (not shown). In use, the plastic sheet is moistened to improve transmission of ultrasound to a rail under test.

Signals $T_{13}$ and $T_{14}$ are routed to RS flipflops 28 and 30 respectively. (RS flipflops 28 and 30 are shown as being constructed of two NAND gates each, but this may be changed.) Thus, when the trailing flank of a negative-going pulse in signal $T_{13}$ arrives at flipflop 28, vertical oscillator 24 is turned on, producing a signal $T_{15}$ with a frequency of 266 KHz.

Signal $T_{15}$ is routed to a counter 32, which in this example counts 16 pulses. After 16 pulses, counter 32 turns flipflop 28 off, which in turn shuts down the vertical oscillator 24.

The operation of monostable multivibrator $M_6$, RS flipflop 30, oblique oscillator 26 and oblique counter 34 is exactly the same, except that oblique oscillator 30 operates at 106 KHz and counter 34 counts to 8.

The measurement board also includes monostable multivibrators $M_7$ and $M_8$ for the shaping of signals $T_9$ and $T_{10}$ which become $T_{17}$ and $T_{18}$ at the outputs, respectively.

The display board has two shift registers 36 and 38, equipped respectively with 16 and 8 outputs. Shift registers 36 and 38 receive, respectively, signals $T_{17}$ and $T_{18}$. Shift registers 36 and 38 are clocked, respectively, by signals $T_{15}$ and $T_{16}$ from oscillators 24 and 26. The rising flanks of signals $T_{13}$, $T_{14}$ from monostable multivibrators $M_5$ and $M_6$ reset the shift registers 36 and 38, respectively, to zero.

As shown in FIG. 3, the shift registers 36 and 38 offset the echo signals by the number of clock pulses which follow them (cf. $T_{19}$ relative to $T_{15}$ and $T_{17}$, as well as $T_{20}$ relative to $T_{16}$ and $T_{18}$). Following the last rising flank of clock signals $T_{15}$ and $T_{16}$, the signals $T_{19}$ and $T_{20}$ remain high until the zero reset by, respectively, $T_{13}$ and $T_{14}$, so that a sufficiently long time elapses to fire a diode selected by the echo signal, as indicated below.

Shift registers 36 and 38 in this example have 16 and 8 outputs respectively, in order to fire one or more LED's by means of buffer registers 40 and 42, the LED's actually fired being those selected by the echo signals of each channel.

In short, the eligibility of an LED for firing is determined by the operation of the oscillator, RS flip-flop, and counter which are associated with the diode array of which the LED is one element. However, firing does not actually take place unless the echo is picked up while that oscillator is operating.

Figure 2:
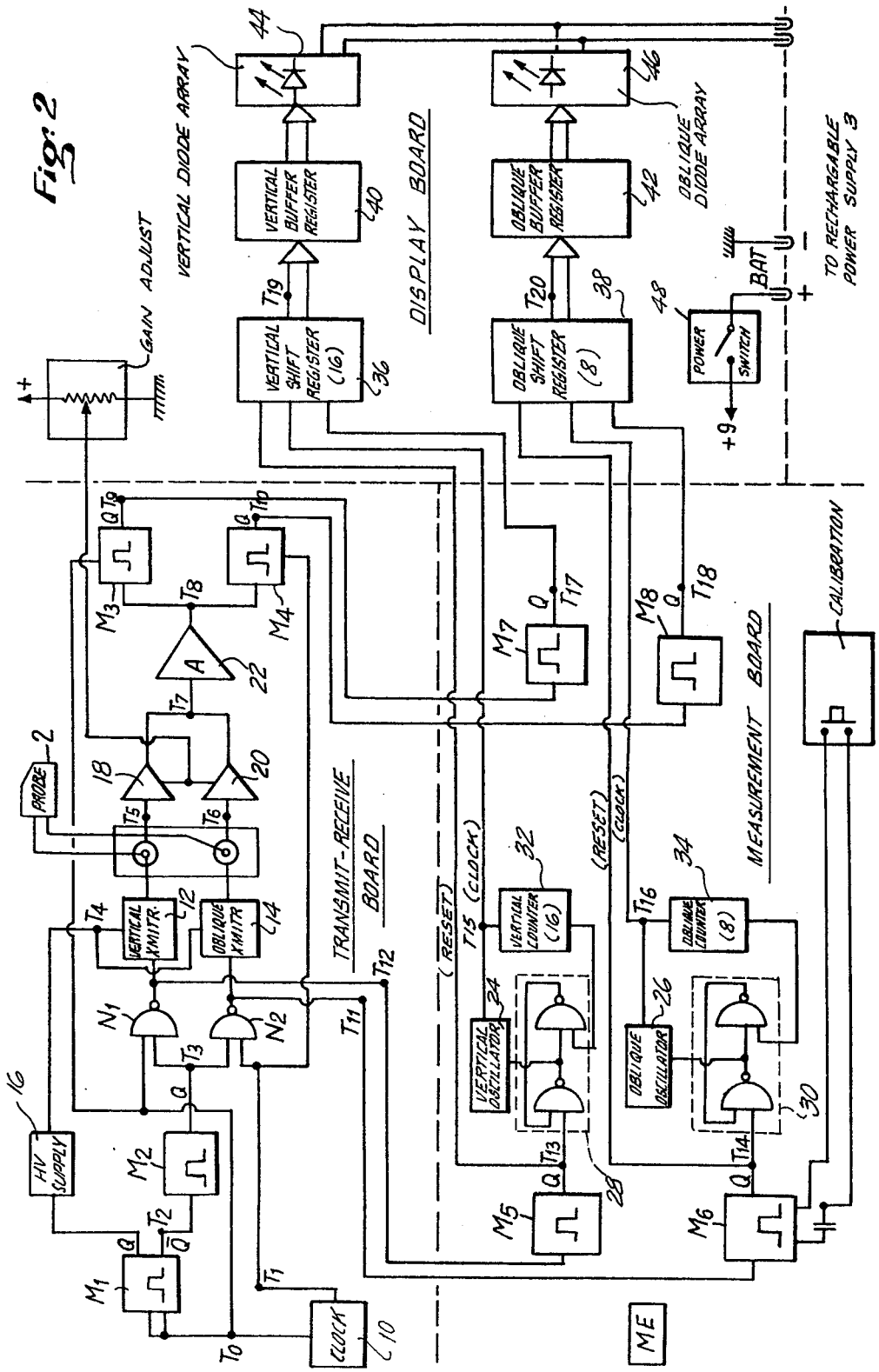
FIG. 2 shows an exemplary schematic diagram of the circuit of the apparatus.

FIG. 2 also shows a power switch 48 connected to the rechargeable power supply. FIG. 2 also shows a calibration button discussed below.

The display and interpretation of the results is shown in FIG. 4.

The display has two arrays, 44 and 46, each formed of a plurality of diodes and disposed vertically (16 diodes) in one case (array 44), and obliquely (8 diodes) in the other (array 46), to display the results simultaneously, by memory storage of the firing of the diodes and, respectively, according to the vertical probing channel and the oblique probing channel.

The sketch in FIG. 4 shows 5 possible positions (A, B, C, D and E) of probe 2 on a rail 5, and the corresponding displays of the diodes in the arrays.

In position A, the display shows a single diode fired in array 44, corresponding to the background echo, i.e. to a display of the height of the rail, e.g. 150 mm.

In position B, the display also shows but a single diode has fired, but that diode is in the middle of array 44, the background echo having disappeared. This display is easily interpreted as the display of a fishplate hole 6.

In position C, several diodes in array 44 fired, again with disappearance of the background echo. This is a case of multiple echoes resulting from a substantially horizontal fissure in the head of the rail.

In position D, the background echo again appears in array 44, and/or the successive firing of diodes in array 46 indicates the presence of transverse fissure in the head of the rail as the probe 2 is moved.

In position E, the disappearance of the background echo, with the firing of no other diode, indicates the presence of a star ring, for example, at the level of a fishplate hole 6'.

To further facilitate interpretation, the diodes at the bottom of array 44 (the last three, for example) and the diodes in the middle (two, for example) may be colored green, while all the others may be orange in order to distinguish displays of rail height and fishplate holes, from a display of a flaw. It is also possible to provide an alarm actuated by certain echo signals in order to attract the attention of the user to the presence of flaws.

A calibration buttom (FIG. 2) may also be provided. This button (here shown for use with the oblique channel) delays signal $T_{16}$ and elongates signal $T_{14}$, by introducing a capacitance in the circuit of monostable multivibrator $M_6$ (see, for example, signals $T_{14}C$ and $T_{16}C$ in FIG. 3).

This makes it possible to fire, in array 46, an LED corresponding to a fishplate hole.

This permits verification of the proper operation of the oblique channel. In the vertical channel, the verification is easily made by visualizing the foot of the rail with the aid of a green diode on the verticle measurement scale.

Many modifications or variations can, of course, be imparted to the embodiment described, without departing from the scope of the invention.

What is claimed is:

1. A method for ultrasonic testing of a body comprising the steps of:

repetitively emitting a first ultrasonic beam into said body in a first direction;

repetitively emitting a second ultrasonic beam alternate with said first ultrasonic beam into said body in a second direction coplanar with said first direction at a predetermined angle thereto;

receiving echoes of said first ultrasonic beam;

displaying said received echoes of said first ultrasonic beam on a first linear display component oriented in a direction corresponding to said first direction;

receiving echoes of said second ultrasonic beam; and displaying said received echoes of said second ultrasonic beam on a second linear display component oriented at substantially at predetermined angle with respect to said first linear display.

2. The process of claim 1, wherein the first and second directions subtend an angle of 70° of arc.

3. The process of claim 1, wherein the body is a rail which is elongated along a third direction, the first, second and third directions are coplaner, and the first direction is perpendicular to the third direction.

4. The process of claims 1 or 3, wherein the first and second display components are linear arrays of light-emitting diodes.

5. An apparatus for the ultrasonic analysis of a body comprising:

a two channel transducer means in ultrasonic transmitting relationship with said body for transmitting alternately first and second beams of ultrasonic sounds into said body, said first beam being transmitted into said body in a first direction, said second beam being transmitted into said body in a second direction coplanar with said first direction and at a predetermined angle with respect thereto;

means coupled to said transducer for receiving echoes of said first and second beams;

evaluation means coupled to said receiving means for evaluating first and second distances from said transducer to an echo generating discontinuity as measured along said first and second direction; and display means coupled to said evaluation means having a first linear display component oriented in a direction corresponding to said first direction and a second linear display component oriented in a direction at substantially said predetermined angle with respect to said first linear display component for simultaneously displaying said first distance on said first linear display and said second distance on said second linear display.

6. The apparatus of claim 5, wherein each of the display components comprises a linear array of light-emitting diodes.

7. The apparatus of claim 6, wherein at least one diode in at least one component is colored differently from other diodes therein.

8. The apparatus of claim 5, further including calibration means for verifying calibration of the evaluation means by activating the evaluation means and causing a display to be displayed on the display means.

9. The apparatus according to claim 5 wherein said transducer means comprises two ultrasonic transducers which convert transmission signals into beams of ultrasound and convert ultrasonic echoes into reception signals.

10. The apparatus of claim 9, wherein the transducer means further comprises an amplification stage which amplifies the transmission and reception signals.

11. The apparatus of claim 10 wherein the amplification stage has an input connected to both transducers through a multiplexer means and an output connected to a demultiplexer means.

12. The apparatus of claim 5, wherein the evaluation means comprises two channels and each channel comprises an oscillator which is turned on after a predetermined delay period has followed transmission of an ultrasonic pulse and which is operated for a predetermined interval.

13. The apparatus of claim 12, wherein each channel in the evaluation means further comprises a shift register which is clocked by the oscillator, coupled to an array of light emitting diodes, and determines which diode in the array will be energized upon detection and receipt of an ultrasonic echo.

* * * * *